United States Patent [19]

Lewis

[11] Patent Number: 4,512,366
[45] Date of Patent: Apr. 23, 1985

[54] SELF-ACTING FLUID NON-RETURN VALVE

[75] Inventor: Jeffrey M. O. Lewis, Charleston, W. Va.

[73] Assignee: The University Court of the University of Edinburgh, Edinburg, Scotland

[21] Appl. No.: 396,686

[22] Filed: Jul. 9, 1982

[30] Foreign Application Priority Data

Jul. 17, 1981 [GB] United Kingdom ............... 8122205

[51] Int. Cl.³ .................. A61F 1/22; F16K 15/03
[52] U.S. Cl. ..................................... 137/527.8; 3/1.5
[58] Field of Search .................. 3/1.5; 137/527, 527.8

[56] References Cited

U.S. PATENT DOCUMENTS

| 215,887 | 5/1979 | Crossman | 137/527.8 |
| 3,352,318 | 11/1967 | Yanowitz | 137/527.8 X |
| 3,448,465 | 6/1969 | Pierce | 137/527.8 |
| 3,726,308 | 4/1973 | Eberhardt | 137/527.8 |
| 3,945,398 | 3/1976 | Masheder | 137/527.8 |
| 4,425,670 | 1/1984 | Figuera | 137/527.8 X |

FOREIGN PATENT DOCUMENTS

| 1327371 | 8/1973 | United Kingdom | 137/527 |
| 1447871 | 9/1976 | United Kingdom | 137/527 |

Primary Examiner—Robert G. Nilson
Attorney, Agent, or Firm—Michael J. Striker

[57] ABSTRACT

A self-acting fluid non-return valve (e.g. a prosthetic heart valve) comprises a flap member located in a smooth bored passage to turn about a pivoting axis between closed and open positions under the influence of pulsing fluid flow through the passage. The pivoting axis divides the flap member into major and minor areas, the former of which is downstream of the axis when the flap member is open to fluid flow. The movement of the flap member is caused by an aerofoil shaping of the flap member which is localized to a part only of the major area.

6 Claims, 11 Drawing Figures

SELF-ACTING FLUID NON-RETURN VALVE

BACKGROUND OF THE INVENTION

Technical Field

This invention relates to a self-acting non-return valve which has particular, but not exclusive, application as a replacement heart valve.

A self-acting non-return valve is described in U.K. Patent Specification Nos. 1327371 and 1447871 and has become known as the 'Edinburgh valve'. An 'Edinburgh valve' employs an aerofoil flap member pivoted in a smooth-bored passage and arranged, under the influence of a fluid flow in one direction through the passage, to turn into an open position in which the valve is substantially aligned with the flow, and on reversal of the flow direction, to turn back through substantially 90° to substantially fully close the passage. The mass distribution of the flap member of an 'Edinburgh valve' is normally substantially balanced about the pivoting axis thereof with the aerofoil shaping facilitating lift of the flap member into its open position once flow past the flap member has occurred due to a small fluid pressure differential being generated across the flap member.

Heretofore, the entire area of the flap member of an 'Edinburgh valve' has been employed to provide the required aerofoil shape and this, together with the requirement that the transverse cross-section of the flap member at the location of the pivoting axis must be adequate to accommodate the pivot means, has set limits on the design of the flap member so that the pressure drop occurring across the flap member in its open position has consistently been higher than would otherwise be desirable.

SUMMARY OF THE INVENTION

According to the present invention a self-acting fluid non-return valve comprises a smooth bored passage, a flap member mounted in the passage to turn about a pivoting axis between a closed position, in which the flap member substantially closes the passage to fluid flow therethrough in a back direction, and an open position in which the flap member is substantially aligned with fluid flow in a reversed, forward direction, the pivoting axis dividing the flap member into a minor area which is upstream of the pivoting axis and a major area which is downstream of the pivoting axis in the open position of the flap member, the major area being shaped to provide an aerofoil cross-section which generates lift in the direction to urge the flap member into the open position in the face of forward direction flow, and is characterised in that the aerofoil cross-section is provided in only (a) localised region(s) of the major area.

In a preferred arrangement, the flap member is substantially circular in plan with the major area occupying some 70% of the plan area of the entire flap member. The aerofoil cross-section is conveniently between 10 and 50% of the plan area of the major area, typically around 25%.

Desirably the pivot means, which define the pivoting axis, are provided in spaced-apart thickened regions of the flap member, the flap member being thinned between these thickened regions. Such a shaping of the flap member in the vicinity of the pivoting axis can dramatically reduce the pressure drop occurring across the valve in the open position of the flap member, since the pressure drop is related to the square of the effective area of the open flap member presented to the flow in the forward direction.

The aerofoil shaping can be obtained by varying the thickness of a part-spherical flap member or by forming a localised recess in a disc of varying thickness.

BRIEF DESCRIPTION OF DRAWINGS

The invention will now be further described, by way of example, with reference to the accompanying drawings, in which.

DESCRIPTION OF PRIOR ART VALVE

Figure 1:
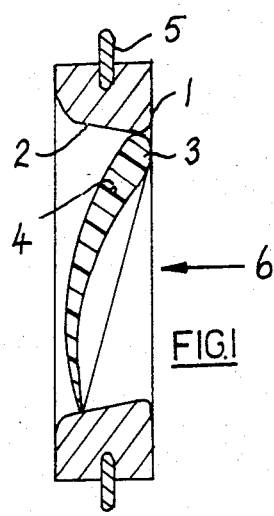
FIG. 1 is sectional side elevation of a conventional 'Edinburgh valve' in the closed position.

The valve shown in FIG. 1 is a prosthetic heart valve having an annular ring 1 defining a smooth passageway 2 with a flap member 3 mounted therein to turn about a pivoting axis 4. A stitching ring 5 permits the valve to be secured in place in a patient's heart in conventional manner. The forward direction of blood flow through the valve is indicated by the arrow 6.

Figure 2B:
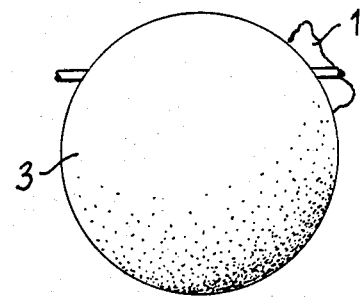
FIGS. 2a and 2b are schematic representations of the flap member of the valve of FIG. 1 seen, respectively, in the forward and backward directions.
Figure 2A:
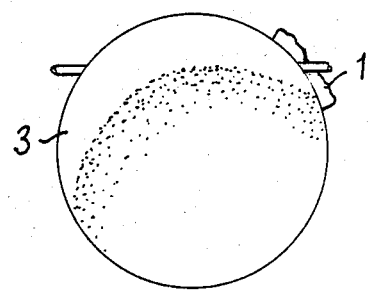
Figure 3A:
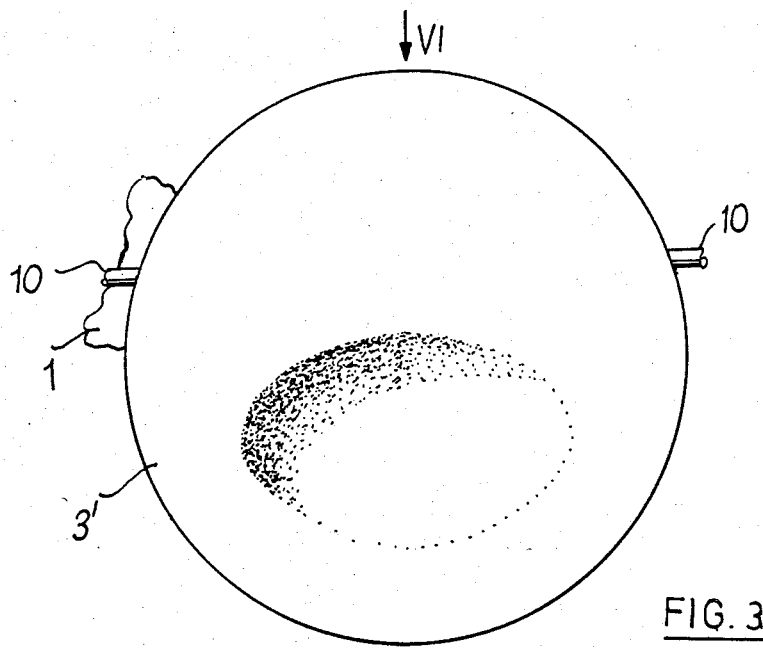
FIGS. 3a and 3b are schematic representations of the flap member of a modified 'Edinburgh valve' according to this invention seen, respectively, in the forward and backward direction.
Figure 3B:
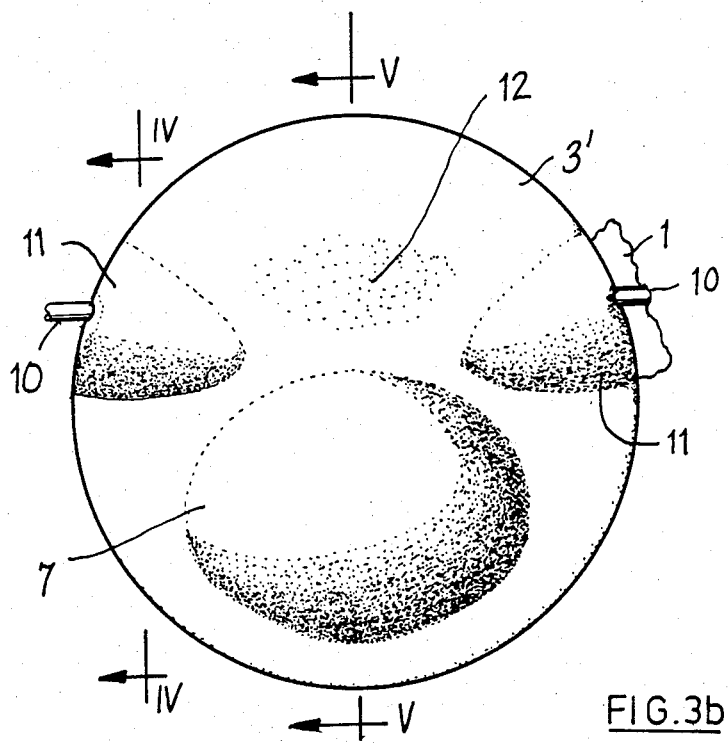
Figure 4:
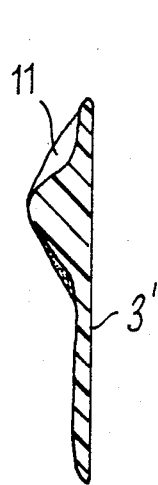
FIGS. 4 and 5 are sections of the lines IV—IV and V—V, respectively, of FIG. 3b.
Figure 5:
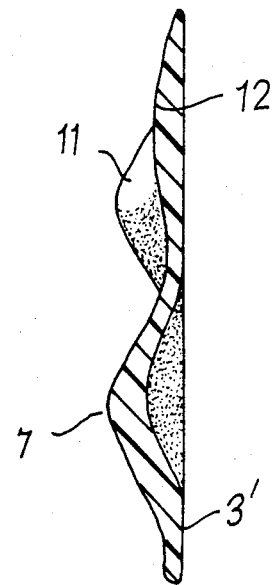
Figure 6:
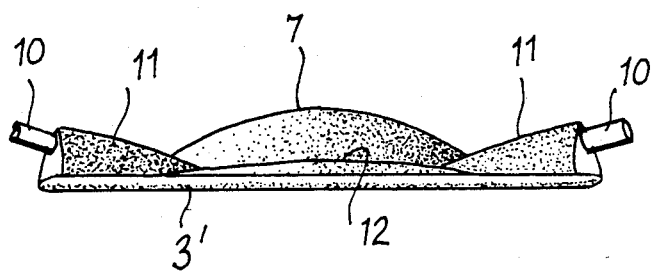
FIG. 6 is an end view of the flap member of FIG. 3a in the direction of the arrow VI.

The entire cross-section of the flap member 3 is utilised to provide an aerofoil cross-section which rapidly lifts the flap member 3 on the appearance of forward flow of blood. This shaping is indicated by FIGS. 2a and 2b and is conventional.

DESCRIPTION OF THE PREFERRED EMBODIMENTS OF INVENTION

FIGS. 3a and 3b and FIGS. 4 to 6 show a modified flap member 3' which can be used in the passageway 2 to give an improved valve. Instead of the entire flap member being contoured to provide an aerofoil section in the flap member 3' this is localised to a region 7 located in the major downstream area of the flap member. From FIG. 5 it can be seen that the region 7 is formed by a localised thickening of a disc which is flat on its upstream side 8 apart from a recess 9. The pivots 10 of the flap member 3' are accommodated in localised thickened regions 11 which leave the central part of the minor downstream area with a gentle convex surface 12.

Figure 7:
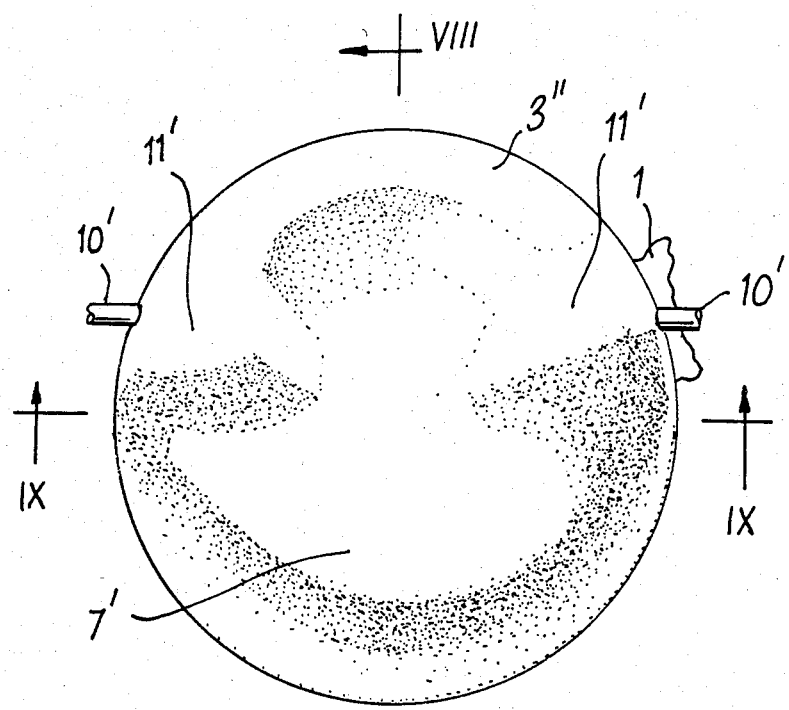
FIG. 7 is a schematic representation of the flap member of a second modified 'Edinburgh valve' according to this invention seen in the backward direction.
Figure 9:
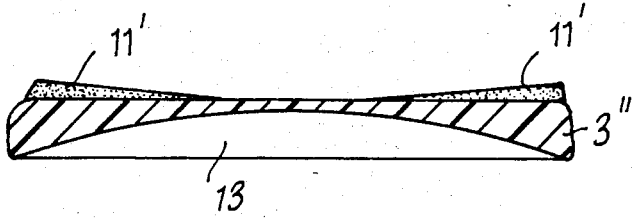
FIGS. 8 and 9 are sections on the lines VIII—VIII and IX—IX of FIG. 7.
Figure 8:
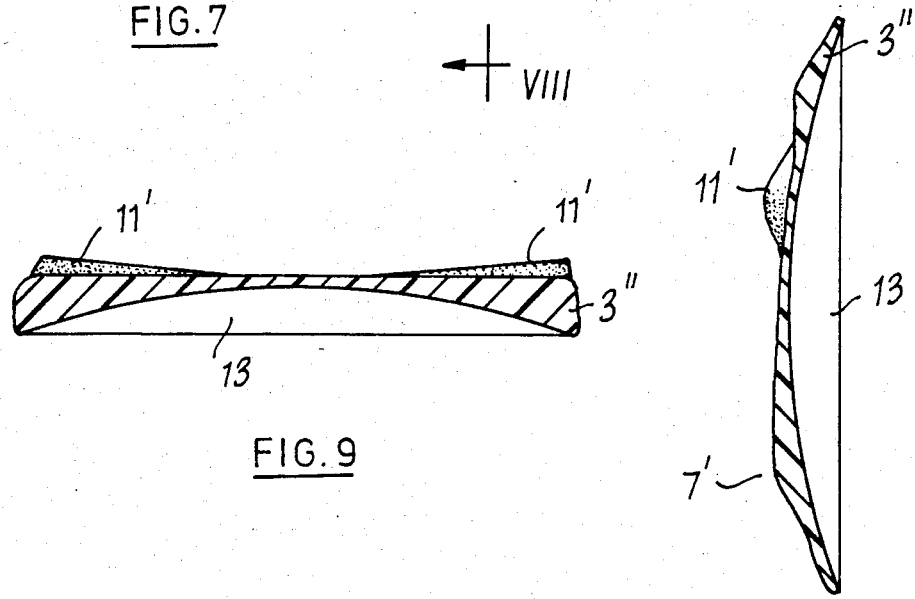

FIGS. 7 to 9 show a second improved flap member 3" which is based on a part spherical cap. On its upstream side it exhibits a concave recess 13 with localised thickening over the region 7' to produce the required "lifting" aerofoil. Thickened regions 11' accommodate the pivots 10'.

ADVANTAGES OF INVENTION

The improved design of flap member employed in a valve in accordance with this invention has the following advantages when compared with a conventional 'Edinburgh valve':

1. The centre of pressure can be positioned at any chosen position downstream of the pivoting axis, simply by forming the aerofoil section at the chosen position.
2. The area of the passageway taken up by the flap member in its open position can be minimized, thus reducing the steady flow pressure drop across the valve.
3. The centre of pressure generating by the aerofoil can be displaced further downstream with respect to the pivoting axis to make the valve open and shut more quickly, thereby reducing the dynamic pressure drop.
4. The flow restriction caused by the pivot means can be reduced, thereby reducing the possibility of a region of slow flow near the pivot means which could be a node for thrombus formation.
5. The extent to which the pivoting axis is offset from a diameter of the flap member can be reduced, thereby allowing a more even distribution of flow between the two sides of the flap member.
6. The lift force generated by the aerofoil section can be tailored to requirements by varying its areal extent as well as the curves used for its construction.
7. The flap member can be made lighter.
8. The efficiency of the modified valve (55% as a typical value) can be closer to the 100% efficiency of an ideal orifice than with a conventional 'Edinburgh valve' (42% as a typical value).

What is claimed is:

1. In a self-acting non-return heart valve including a ring member defining a smooth bored passage, a flap member mounted in the ring member to turn by pivot means within the passage about a pivoting axis between a closed position, in which the flap member substantially closes the passage to blood flow therethrough in a first back direction, and an open position in which the flap member is substantially aligned with blood flow in a second forward direction being reverse to said first direction, the pivoting axis dividing the flap member into a minor area which is upstream, with reference to blood flow, of the pivoting axis and a major area which is downstream, with reference to blood flow, of the pivoting axis in the open position of the flap member the major area being shaped to provide an aerofoil cross-section to the flap member which generates lift in the direction to urge the flap member into the open position in the face of the second direction flow, wherein the improvement comprises said flap member being a relatively thin flap having at least one thickened localized region in said major area removed from said pivot means responsible for generating the lift, leaving only said pivot means and said localized region thickened while the remaining part of said flap remains relatively thin.

2. A self-acting heart valve as claimed in claim 1, in which the flap member is substantially circular in plan with the major area occupying substantially 70% of the plan area of the entire flap member.

3. A self-acting heart valve as claimed in claim 2, in which the localized region constitutes between 10 an 50% of the plan area of said major area.

4. A self-acting heart valve as claimed in claim 2, in which the localized region constitutes substantially 25% of the plan area of said major area.

5. A self-acting heart valve as claimed in claim 1, in which the pivot means, which define the pivoting axis, are provided in spaced-apart thickened regions of the flap member, the flap member being thinned between these thickened regions.

6. A self-acting heart valve as claimed in claim 5, in which the aerofoil shaping is obtained by varying the thickness of the localized region of a part-spherical flap member.

* * * * *